US008703204B2

(12) United States Patent
Bloom et al.

(10) Patent No.: US 8,703,204 B2
(45) Date of Patent: Apr. 22, 2014

(54) NANOPARTICLES COMPRISING A CHOLESTERYL ESTER TRANSFER PROTEIN INHIBITOR AND A NON-IONIZABLE POLYMER

(75) Inventors: Corey Jay Bloom, Bend, OR (US); Marshall David Crew, Bend, OR (US); Daniel Tod Smithey, Bend, OR (US); Warren Kenyon Miller, Bend, OR (US); Michael Mark Morgen, Bend, OR (US)

(73) Assignee: Bend Research, Inc., Bend, OR (US)

( * ) Notice: Subject to any disclaimer, the term of this patent is extended or adjusted under 35 U.S.C. 154(b) by 784 days.

(21) Appl. No.: 12/451,288

(22) PCT Filed: Apr. 23, 2008

(86) PCT No.: PCT/IB2008/001145
§ 371 (c)(1),
(2), (4) Date: Nov. 3, 2009

(87) PCT Pub. No.: WO2008/135855
PCT Pub. Date: Nov. 13, 2008

(65) Prior Publication Data
US 2010/0129447 A1    May 27, 2010

Related U.S. Application Data

(60) Provisional application No. 60/915,698, filed on May 3, 2007.

(51) Int. Cl.
*A61K 9/14* (2006.01)
*A61K 9/51* (2006.01)

(52) U.S. Cl.
USPC ........... 424/495; 424/489; 424/490; 424/491; 424/501

(58) Field of Classification Search
USPC ................................................ 424/465–489
See application file for complete search history.

(56) References Cited

U.S. PATENT DOCUMENTS

| | | |
|---|---|---|
| 3,960,757 A | 6/1976 | Morishita et al. |
| 4,107,288 A | 8/1978 | Oppenheim et al. |
| 4,158,707 A | 6/1979 | Steffen |
| 4,229,360 A | 10/1980 | Schneider |
| 4,298,594 A | 11/1981 | Sears |
| 4,329,332 A | 5/1982 | Couvreur et al. |
| 4,331,654 A | 5/1982 | Morris |
| 4,501,726 A | 2/1985 | Schroder |
| 4,610,868 A | 9/1986 | Fountain et al. |
| 4,615,881 A | 10/1986 | Deibig et al. |
| 4,639,370 A | 1/1987 | Carli |
| 4,649,155 A | 3/1987 | Steffen |
| 4,725,442 A | 2/1988 | Haynes |
| 4,728,513 A | 3/1988 | Ventouras |
| 4,731,210 A | 3/1988 | Weder et al. |
| 4,754,027 A | 6/1988 | Applegren |
| 4,826,689 A | 5/1989 | Violanto |
| 4,830,858 A | 5/1989 | Payne |
| 4,837,381 A | 6/1989 | Steber et al. |
| 4,880,634 A | 11/1989 | Speiser |
| 4,882,164 A | 11/1989 | Ferro et al. |
| 4,904,479 A | 2/1990 | Illum |
| 4,917,900 A | 4/1990 | Jones et al. |
| 4,997,454 A | 3/1991 | Violante |
| 5,049,322 A | 9/1991 | Devissaguet et al. |
| 5,051,261 A | 9/1991 | McGinity |
| 5,084,278 A | 1/1992 | Mehta |
| 5,085,864 A | 2/1992 | Cannon et al. |
| 5,091,187 A | 2/1992 | Haynes |
| 5,091,188 A | 2/1992 | Haynes |
| 5,112,621 A | 5/1992 | Stevens et al. |
| 5,118,528 A | 6/1992 | Fessi et al. |
| 5,133,908 A | 7/1992 | Stainmesse et al. |
| 5,145,684 A | 9/1992 | Liversidge et al. |
| 5,152,923 A | 10/1992 | Weder |
| 5,174,930 A | 12/1992 | Stainmesse et al. |
| 5,188,837 A | 2/1993 | Domb |
| 5,202,159 A | 4/1993 | Chen et al. |
| 5,298,262 A | 3/1994 | Na |
| 5,302,401 A | 4/1994 | Liversidge et al. |
| 5,314,506 A | 5/1994 | Midler et al. |
| 5,336,507 A | 8/1994 | Na |
| 5,340,591 A | 8/1994 | Nakano et al. |
| 5,352,459 A | 10/1994 | Hollister et al. |
| 5,370,880 A | 12/1994 | Jones et al. |
| 5,445,830 A | 8/1995 | Ishizue et al. |

(Continued)

FOREIGN PATENT DOCUMENTS

| | | |
|---|---|---|
| EP | 877033 A1 | 11/1998 |
| EP | 1180062 B1 | 3/2004 |

(Continued)

OTHER PUBLICATIONS

Al-Kassas, R., "Design and In Vitro Evaluation of Gentamicin-Eudragit Microspheres Intended for Intra-Ocular Administration," Journal of Microencapsulation, 21:1(2004)71-81.
Amrite, A.C., S.P. Ayalasomayajula, and U. Kompella, "Ocular Distribution of Intact Nano- and Micro Particles Following Subconjunctival and Systemic Routes of Administration," Drug Delivery Techn., vol. 2, No. 3, 2003.
Barbu, E., L. Verestiuc, T.G. Nevell, and J. Tsibouldis, "Polymeric Materials for Ophthalmic Drug Delivery: Trends and Perspectives," J. of Materials Chemistry, 16(2006)3439-3443.
Bodmeier et al., "Preparation and Evaluation of Drug-Containing Polymeric Nanosuspensions," presented at the 5th International Conference on Pharmaceutical Technology, Paris, France, 1989. Proceedings vol. 2, pp. 265-268.

(Continued)

*Primary Examiner* — Michael G Hartley
*Assistant Examiner* — Micah-Paul Young
(74) *Attorney, Agent, or Firm* — Chernoff Vilhauer McClung & Stenzel LLP

(57) ABSTRACT

A pharmaceutical composition comprises nanoparticles comprising a cholesteryl ester transfer protein inhibitor and a poorly aqueous soluble non-ionizable polymer.

15 Claims, No Drawings

(56) References Cited

U.S. PATENT DOCUMENTS

| | | |
|---|---|---|
| 5,456,923 A | 10/1995 | Nakamichi et al. |
| 5,470,583 A | 11/1995 | Na |
| 5,484,608 A | 1/1996 | Rudnic et al. |
| 5,494,683 A | 2/1996 | Liversidge et al. |
| 5,510,118 A | 4/1996 | Bosch et al. |
| 5,534,270 A | 7/1996 | De Castro |
| 5,543,158 A | 8/1996 | Gref et al. |
| 5,552,160 A | 9/1996 | Liversidge et al. |
| 5,556,642 A | 9/1996 | Kobayashi et al. |
| 5,560,931 A | 10/1996 | Eickhoff et al. |
| 5,560,932 A | 10/1996 | Bagchi et al. |
| 5,565,188 A | 10/1996 | Wong et al. |
| 5,565,215 A | 10/1996 | Gref et al. |
| 5,569,448 A | 10/1996 | Wong et al. |
| 5,569,469 A | 10/1996 | Lovrecich |
| 5,571,536 A | 11/1996 | Eickhoff et al. |
| 5,573,783 A | 11/1996 | Desieno |
| 5,576,016 A | 11/1996 | Amselem |
| 5,578,325 A | 11/1996 | Domb et al. |
| 5,585,108 A | 12/1996 | Ruddy et al. |
| 5,622,938 A | 4/1997 | Wong |
| 5,662,883 A | 9/1997 | Bagchi et al. |
| 5,662,932 A | 9/1997 | Amselem |
| 5,665,277 A | 9/1997 | Johnson et al. |
| 5,665,331 A | 9/1997 | Bagchi et al. |
| 5,667,800 A | 9/1997 | De Vringer |
| 5,679,690 A | 10/1997 | Andre et al. |
| 5,683,723 A | 11/1997 | Spenlehauer et al. |
| 5,705,196 A | 1/1998 | Galan Valdivia et al. |
| 5,707,634 A | 1/1998 | Schmitt |
| 5,716,642 A | 2/1998 | Bagchi et al. |
| 5,718,919 A | 2/1998 | Ruddy |
| 5,780,062 A | 7/1998 | Frank et al. |
| 5,783,211 A | 7/1998 | Manzo et al. |
| 5,785,976 A | 7/1998 | Westesen |
| 5,834,025 A | 11/1998 | de Garavilla et al. |
| 5,843,509 A | 12/1998 | Calvo Salve et al. |
| 5,853,753 A | 12/1998 | Maierhofer et al. |
| 5,874,111 A | 2/1999 | Maitra et al. |
| 5,885,486 A | 3/1999 | Westesen |
| 5,889,051 A | 3/1999 | Chen et al. |
| 5,919,408 A | 7/1999 | Muller et al. |
| 5,932,249 A | 8/1999 | Gruber et al. |
| 5,935,939 A | 8/1999 | Kararli et al. |
| 5,952,005 A | 9/1999 | Olsson et al. |
| 5,968,551 A | 10/1999 | Oshlack |
| 6,007,845 A | 12/1999 | Domb et al. |
| 6,020,004 A | 2/2000 | Shah |
| 6,027,747 A | 2/2000 | Terracol |
| 6,083,529 A | 7/2000 | Manzo et al. |
| 6,139,870 A | 10/2000 | Verrecchia |
| 6,143,211 A | 11/2000 | Mathiowitz et al. |
| 6,146,663 A | 11/2000 | Bissery et al. |
| 6,153,225 A | 11/2000 | Lee |
| 6,177,103 B1 | 1/2001 | Pace et al. |
| 6,197,348 B1 | 3/2001 | Morella et al. |
| 6,197,349 B1 | 3/2001 | Westesen |
| 6,207,178 B1 | 3/2001 | Westesen |
| 6,217,901 B1 | 4/2001 | Perrott |
| 6,235,224 B1 | 5/2001 | Mathiowitz et al. |
| 6,245,349 B1 | 6/2001 | Yiv et al. |
| 6,254,889 B1 | 7/2001 | Kigoshi et al. |
| 6,267,985 B1 | 7/2001 | Chen |
| 6,267,989 B1 | 7/2001 | Liversidge et al. |
| 6,268,053 B1 | 7/2001 | Woiszwillo et al. |
| 6,270,806 B1 | 8/2001 | Liversidge |
| 6,280,770 B1 | 8/2001 | Pather et al. |
| 6,303,560 B1 | 10/2001 | Hartan et al. |
| 6,361,944 B1 | 3/2002 | Mirkin et al. |
| 6,375,986 B1 | 4/2002 | Ryde |
| 6,383,500 B1 | 5/2002 | Wooley et al. |
| 6,391,338 B1 | 5/2002 | Frisbee et al. |
| 6,406,745 B1 | 6/2002 | Talton |
| 6,428,814 B1 | 8/2002 | Bosch et al. |
| 6,440,458 B1 | 8/2002 | Yamashita et al. |
| 6,443,898 B1 | 9/2002 | Unger et al. |
| 6,447,806 B1 | 9/2002 | Gassmann |
| 6,458,383 B2 | 10/2002 | Chen et al. |
| 6,462,093 B1 | 10/2002 | Miyamoto |
| 6,479,146 B1 | 11/2002 | Caruso et al. |
| 6,485,743 B1 | 11/2002 | Jung et al. |
| 6,509,034 B1 | 1/2003 | Calanchi et al. |
| 6,517,859 B1 | 2/2003 | Tice et al. |
| 6,537,579 B1 | 3/2003 | Desai et al. |
| 6,544,497 B2 | 4/2003 | Zhu et al. |
| 6,548,264 B1 | 4/2003 | Tan et al. |
| 6,551,619 B1 | 4/2003 | Penkler et al. |
| 6,555,139 B2 | 4/2003 | Sharma |
| 6,565,873 B1 | 5/2003 | Shefer |
| 6,565,875 B2 | 5/2003 | Tice et al. |
| 6,565,885 B1 | 5/2003 | Tarara et al. |
| 6,576,264 B1 | 6/2003 | Henriksen et al. |
| 6,579,519 B2 | 6/2003 | Maitra et al. |
| 6,592,899 B2 | 7/2003 | Fowers et al. |
| 6,592,901 B2 | 7/2003 | Durig et al. |
| 6,592,903 B2 | 7/2003 | Ryde |
| 6,596,262 B2 | 7/2003 | Zhu et al. |
| 6,596,311 B1 | 7/2003 | Dobetti |
| 6,607,784 B2 | 8/2003 | Kipp et al. |
| 6,616,869 B2 | 9/2003 | Mathiowitz et al. |
| 6,620,351 B2 | 9/2003 | Gupta |
| 6,623,761 B2 | 9/2003 | Hassan |
| 6,632,671 B2 | 10/2003 | Unger |
| 6,638,537 B2 | 10/2003 | Dennis et al. |
| 6,638,621 B2 | 10/2003 | Anderson |
| 6,638,994 B2 | 10/2003 | Crooks et al. |
| 6,645,517 B2 | 11/2003 | West et al. |
| 6,645,569 B2 | 11/2003 | Cramer et al. |
| 6,649,192 B2 | 11/2003 | Alonso Fernandez et al. |
| 6,652,967 B2 | 11/2003 | Yadav et al. |
| 6,656,504 B1 | 12/2003 | Bosch et al. |
| 6,656,507 B2 | 12/2003 | Petereit et al. |
| 6,656,984 B1 | 12/2003 | Haasmaa et al. |
| 6,660,382 B2 | 12/2003 | Nouri et al. |
| 6,663,885 B1 | 12/2003 | Hager et al. |
| 6,669,959 B1 | 12/2003 | Adjei et al. |
| 6,677,386 B1 | 1/2004 | Giezen et al. |
| 6,682,761 B2 | 1/2004 | Pace |
| 6,682,895 B2 | 1/2004 | Mirkin et al. |
| 6,685,960 B1 | 2/2004 | Gasco |
| 6,692,769 B1 | 2/2004 | Ishibashi et al. |
| 6,696,084 B2 | 2/2004 | Pace et al. |
| 6,709,622 B2 | 3/2004 | Billiet |
| 6,720,008 B2 | 4/2004 | Allison |
| 6,726,934 B1 | 4/2004 | Prokop |
| 6,746,635 B2 | 6/2004 | Mathiowitz et al. |
| 6,755,915 B1 | 6/2004 | Van Soest et al. |
| 6,756,062 B2 | 6/2004 | Johnston et al. |
| 6,761,903 B2 | 7/2004 | Chen et al. |
| 6,780,324 B2 | 8/2004 | Le Garrec et al. |
| 6,793,938 B2 | 9/2004 | Sankaram |
| 6,824,791 B2 | 11/2004 | Mathiowitz et al. |
| 6,827,946 B2 | 12/2004 | Hirsh |
| 6,863,914 B1 | 3/2005 | Auweter et al. |
| 6,869,617 B2 | 3/2005 | Kipp et al. |
| 6,878,693 B2 | 4/2005 | Goldshtein |
| 6,887,493 B2 | 5/2005 | Shefer |
| 6,890,512 B2 | 5/2005 | Roser et al. |
| 7,081,450 B2 | 7/2006 | Goldshtein |
| 7,105,176 B2 | 9/2006 | Auweter et al. |
| 2002/0012675 A1 | 1/2002 | Jain et al. |
| 2002/0054914 A1 | 5/2002 | Morcol |
| 2002/0068092 A1 | 6/2002 | Bosch et al. |
| 2002/0081334 A1 | 6/2002 | Johnston et al. |
| 2002/0106403 A1 | 8/2002 | Parikh et al. |
| 2002/0127278 A1 | 9/2002 | Kipp et al. |
| 2002/0142017 A1 | 10/2002 | Simonnet |
| 2003/0003155 A1 | 1/2003 | Kipp et al. |
| 2003/0026844 A1 | 2/2003 | Lee et al. |
| 2003/0031719 A1 | 2/2003 | Kipp et al. |
| 2003/0049323 A1 | 3/2003 | Hitt et al. |
| 2003/0072801 A1 | 4/2003 | Curatolo et al. |
| 2003/0095928 A1 | 5/2003 | McGurk et al. |
| 2003/0129239 A1 | 7/2003 | Goldshtein |

(56) References Cited

U.S. PATENT DOCUMENTS

| | | | |
|---|---|---|---|
| 2003/0147965 A1 | 8/2003 | Bassett et al. | |
| 2003/0166509 A1 | 9/2003 | Edwards et al. | |
| 2003/0170309 A1 | 9/2003 | Babcock et al. | |
| 2003/0190347 A1 | 10/2003 | Supersaxo et al. | |
| 2003/0198674 A1* | 10/2003 | Curatolo et al. | 424/468 |
| 2003/0206949 A1 | 11/2003 | Parikh et al. | |
| 2003/0235619 A1 | 12/2003 | Allen et al. | |
| 2004/0009229 A1 | 1/2004 | Unger et al. | |
| 2004/0013613 A1 | 1/2004 | Jain et al. | |
| 2004/0018229 A1 | 1/2004 | Henriksen et al. | |
| 2004/0018236 A1 | 1/2004 | Gurny et al. | |
| 2004/0047913 A1 | 3/2004 | Allemann et al. | |
| 2004/0067251 A1 | 4/2004 | Johnston et al. | |
| 2004/0071776 A1 | 4/2004 | Boudy et al. | |
| 2004/0091546 A1 | 5/2004 | Johnson | |
| 2004/0180005 A1 | 9/2004 | Jurgens | |
| 2004/0191319 A1 | 9/2004 | Yun | |
| 2004/0220081 A1 | 11/2004 | Kreitz et al. | |
| 2004/0245662 A1 | 12/2004 | Chaubal et al. | |
| 2004/0247624 A1 | 12/2004 | Unger et al. | |
| 2005/0013866 A1 | 1/2005 | Maincent et al. | |
| 2005/0038007 A1* | 2/2005 | Curatolo et al. | 514/171 |
| 2005/0238716 A1 | 10/2005 | Verrijk et al. | |
| 2006/0134220 A1 | 6/2006 | Aboubakar et al. | |

FOREIGN PATENT DOCUMENTS

| | | |
|---|---|---|
| EP | 710261 B1 | 5/2004 |
| WO | WO 9710811 A1 | 3/1997 |
| WO | WO 9713503 A1 * | 4/1997 |
| WO | WO 9933558 A1 | 7/1999 |

OTHER PUBLICATIONS

Bodmeier, et al., "Indomethacin Polymer Nanosuspension Prepared by Microfluidization", Journal of Controlled Release, 12 (1990) 223-233.

Bourges, J.-L., S.E. Gautier, F. Delie, R.A. Bejjani, J.-C. Jeanny, R. Gurny, D. BenEzra, and F.F. Behar-Cohen, "Ocular Drug Delivery Targeting the Regina and Retinal Pigment Epithelium Using Polylactide Nanoparticles," Investigative Ophthalmology and Visual Science, 44:8(2003)3562-3569.

Briancon, S., H. fessi, F. Lecomet, and J. Lieto, "Study and Scale-Up of a Nanoprecipitation Process," Industrial Crystallization 1999 (IChemE), pp. 1-10.

Bucolo, C., A. Maltese, F. Maugeri, B. Busa, G. Puglisi, and R. Pignatello, "Eudragit RL100 Nanoparticle System for the Ophthalmic Delivery of Cloricromene," Journal of Pharmacy and Pharmacology, 56(2004)841 846.

Calvo, P., J.L. Vila-Jato, and M.J. Alonso, "Evaluation of Cationic Polymer-Coated Nanocapsules as Ocular Drug Carriers," International Journal of Pharmaceutics, 153(1997)41-50.

Carrasquillo, K.G., J.A. Ricker, I.K. Rigas, J.W. Miller, E.S. Gragoudas, and A.P. Adamis, "Controlled Delivery of the Anti-VEGF Aptamer EYE001 with Poly(lactic-co-glycolic) Acid Microspheres," Investigative Ophthalmology and Visual Science, 44:1(2003)290-299.

Cavalli, R., M.R. Gasco, P. Chetoni, S. Burgalassi, and M.F. Saettone, "Solid Lipid Nanoparticles (SLN) as Ocular Delivery System for Tobramycin," International J. Pharmaceutics, 238(2002)241-245.

Chen et al., "Comparison of Albumin and Casein Microspheres as a Carrier for Doxorubicin," J. Pharm. Pharmacol.39(1987)978-985.

Chiou, W.L., and S.Riegelman, J. Pharm. Sci., 60:9(1971)1281-1302.

Couvreur, Microspheres and Drug Therapy, Elsevier, (1984) pp. 103-115.

De, T.K., D.J. Rodman, B.A. Holm, P.N. Prasad, and E.J. Bergey, "Brimonidine Formulation in Polyacrylic Acid Nanoparticles for Ophthalmic Delivery," J. Microencapsualtion, 20:3(2003)361-374.

Decampos, A.M., A. Sanchez, and M.J. Alonso, "Chitosan Nanoparticles: A New Vehicle for the Improvement of the Delivery of Drugs to the Ocular Surface. Application to Cyclosporin A," International J. of Pharmaceutics, 224(2001)159-168.

Decampos., A.M., A. Sanchez, R. Gref, P. Calvo, and M.J. Alonso, "The Effect of a PGE Versus a Chitosan Coating on the Interaction of Drug Colloidal Carriers with the Ocular Mucosa," European Journal of Pharmaceutical Sciences, 20(2003)73-81.

Dejaeghere, F., E. Allemann, J.-C. Leroux, W. Stevels, J. Feijen, E. Doelker, and R. Gurny, "Formulation of Lyoprotection of Poly(Lactic Acid-Co-Ethylene Oxide) Nanoparticles: Influence on Physical Stability and in Vitro cell Uptake," Pharmaceutical Research, 16:6(1999)859-866.

Desai, S.D., and J. Blanchard, "Pluronic F127-Based Ocular Delivery System Containing Biodegradable Polyisobutylcyanoacrylate Nanocapsules of Pilocarpine," Drug Delivery, 7(2000)201-207.

Fee, C.A., and R.I. Pettigrew, "National Institute of Biomedical Imaging and Bioengineering: Poised for the Future," National Institute of Biomedical Imaging and Bioengineering, 229:3(2003)636-637.

Fessi, H., F. Puisieux, J.Ph. Devissaguet, N. Ammoury, and S. Benita, "Nanocapsule Formation by Interfacial Polymer Deposition Following Solvent Displacement," International J. of Pharmaceutics, 55(1989)R1-R4.

Ford, J.L., Pharm. Acta Helv., 61:3(1986)69-87.

Fox et al., from Proteins in Food Processing, R.Y. Yada (ed), CRC Press, 2004, Chapter 3: The Caseins pp. 29-71.

Gavini, E., P. Chetoni, M. Cossu, M.G. Alvarez, M.F. Saettone, and P. Giunchedi, "PLGA Microspheres for the Ocular Delivery of a Peptide Drug, Vancomycin Using Emulsification/Spray-Drying as the Preparation Method: In Vitro/In Vivo Studies," European Journal of Pharmaceutics and Biopharmaceutics, 57(2004)207-212.

Giannavola, C., C. Bucolo, A. Maltese, D. Paolino, M.A. Vandelli, G. Puglisi, V.H.L. Lee, and M. Fresta, "Influence of Preparation Conditions on Acyclovir-Loaded Poly-d,l-Lactic Acid Nanospheres and Effect of PEG Coating on Ocular Drug Bioavailability." Pharmaceutical Research, 20:4(2003)584-590.

Gurny, Drug Develop. Ind. Pharm. 7(1), 1-25, 1981.

Gurny, R., T. Boye, and H. Ibrahim, "Ocular Therapy with Nanoparticulate Systems for Controlled Drug Delivery," Journal of Controlled Release, 2(1985)353-361.

Harmia, J. Microencapsulation, 1986 vol. 3, No. 1, p. 3-12.

Hasegawa, H., et al., Chem. Pharm. Bull., 33:4(1985)1615-1619; Chem. Pharm. Bull., 34:5(1986)2183-2190; Chem. Pharm. Bull., 36:12(1988) 4941-4950.

Herrero-Vanrell, R., and M.F. Refojo, "Biodegradable Microspheres for Vitreoretinal Drug Delivery," Advanced Drug Delivery Reviews, 52(2001)5 16.

Hornig et al., "Novel Nanoparticles Based on Dextran Esters with Unsaturated Moieties," Macromolecular Rapid Commun., 2005, 26, 1908-1912.

Hornig et al., "Structure Design of Multifunctional Furoate and Pyroglutamate Esters of Dextran by Polymer-Analogous Reactions," Macromol. Biosci. 2007, 7, 297-306.

Hsiue, G.-H., S.-H. Hsu, C.-C. Yang, S.-H. Lee,a nd I.-K. Yang, "Preparation of Controlled Release Ophthalmic Drops, for Glaucoma Therapy Using Thermosensitive poly-N-Isopropylacrylamide," Biomaterials, 23(2002)457 462.

Kim, S., Y.T. Lim, E.G. Soltesz, A.M. DeGrand, J. Lee, A. Nakayama, J.A. Parker, T. Mihaljevic, R.G. Laurence, D.M. Dor, L.H. Cohn, M.G. Bawendi, and J.V. Frangioni,"Near-Infrared Fluorescent Type II Quantum Dots for Sentinel Lymph Node Mapping," Nature Biotechnology, 22:1(2004)93-97.

Knepp et al., Synthesis, Properties, and Intratumoral Evaluation of Mitoxantrone-Loaded Casein Microspheres in Lewis Lung Carcinoma, J. Pharm. Pharmacol., 45(1993)887-891.

Kompella, U.B., N. Bandi, and S.P. Ayalasomayajula, "Subconjunctival Nano- and Microparticles Sustain Retinal Delivery of Budesonide, A Corticosteroid Capable of Inhibiting VEGF Expression," Investigative Ophthalmology and Visual Science, 44:3(2003)1192-1201.

Kumar, M.N.V., "Nano and Microparticles as Controlled Drug Delivery devices," J. Pharm. Pharmaceutical Sciences, 3:2(2000)234-258.

(56) References Cited

OTHER PUBLICATIONS

Latha et al., Casein as a Carrier Matrix for 5-Fluorouracil: Drug Release from Microspheres, Drug-Protein Conjugates and In-Vivo Degradation of Microspheres in Rat Muscle, J. Pharm. Pharmacol., 46(1994)858-862.
Latha et al., Glutaraldehyde Cross-Linked Bovine Casein Microspheres as a Matrix for the Controlled Release of Theophylline: In Vitro Studies, J. Pharm. Pharmacol., 46(1994)8-13.
Latha et al., Progesterone Release from Glutaraldehyde Cross-Linked Casein Microspheres: In Vitro Studies and In Vivo Response in Rabbits, Contraception, 61(2000)329-334.
Lecorre, P., J.H. Rytting, V. Gajan, F. Chevanne, and R. LeVerge, "In Vitro Controlled Release Kinetics of Local Anaesthetics from Poly(D,L-lactice) and Poly (lactice-co-glycolide) Microspheres," Journal of Microencapsulation, 1997, pp. 243-255.
Lellemand, F., O. Felt-Baeyens, K. Besseghir, F. Behar-Cohen, and R. Gurny, "Cyclosporine a Delivery to the Eye: A Pharmaceutical Challenge," European J. of Pharmaceutics and Biopharmaceutics, 56(2003)307 318.
Lemarchand, C., R. Gref, and P. Couvreur, "Polysaccharide-Decorated Nanoparticles," European J. of Pharmaceutics and Biopharmaceutics, 58(204,327-341, Jun. 19 2004.
Lemarchand, et al., "Influence of polysaccharide coating on the interactions of nanoparticles with biological systems," Biomaterials, 27(2006)108-118.
Liebert, et al., "Nanoparticles on the Basis of Highly Functionalized Dextrans," J. Am. Chem. Soc. 2005, 127, 10484-10485.
Longmuir, K.J., R.T. Robertson, S.M. Haynes, J.L. Baratta, and A.J. Waring, "Effective Targeting of Liposomes to Liver and Hepatocytes In Vivo by Incorporation of a Plasmodium Amino Acid Sequence," Pharmaceutical Research, 23:4(2006)759-769.
Losa, C., L. Marchal-Heussler, F. Orallo, J.L. Vila Jato, and M.J. Alonso, "Design of New Formulations for Topical Ocular Administration: Polymeric Nanocapsules Containing Metipranolol," Pharmaceutical Research, 10:1(1993)80-87.
Merodio, M., J.M. Irache, F. Valamanesch, and M. Mirshahi, "Ocular Disposition and Tolerance of Ganciclovir-Loaded Albumin Nanoparticles after Intravitreal Injection in Rats," Biomaterials, 23(2002)1587-1594.
Mirshahi et al., Development of Drug Delivery Systems from Vegetal Proteins: Legumin Nanoparticles, Drug Dev. Indust.Pharm., 22:8(1996)841-846.
Mora-Gutierrez et al., Modeling Calcium-Induced Solubility in Caprine Milk Caseins Using a Thermodynamic Linkage Approach, J. Dairy Sci., 76(1993)3698-3710.
Ohio State FST 822 Class Lecture, Casein, 2006, 5 pp.
Pignatello, R., C. Bucolo, and G. Puglisi, "Ocular Tolerability of Eudragit RS100 and RL100 Nanosuspensions as Carriers for Ophthalmic Controlled Drug Delivery," Journal of Pharmaceutical Sciences, 91:12(2002)2636-2641.
Pignatello, R., C. Bucolo, G. Spedalieri, A. Maltese, and G. Puglisi, "Flurbiprofen-Loaded Acrylate Polymer Nanosuspensions for Ophthalmic Application," Biomaterials, 23(2002)3247-3255.
Pignatello, R., C. Bucolo, P. Ferra, A. Maltese, A. Puleo, and G. Puglisi, "Eudragit RS100 Nanosuspensions for the Ophthalmic Controlled Delivery of Ibuprofen," European Journal of Pharmaceutical Sciences, 16(2002)53 61.
Qaddoumi, M.G., H. Ueda, J. Yang, J. Davda, V. Labhasetwar, and V.H.L. Lee, "The Characteristics and Mechanisms of Uptake of PLGA Nanoparticles in Rabbit Conjuctival Epithelial Cell Layers," Pharmaceutical Research, 21:4(2004)641-648.
Raveendran, P, J. Fu, and S.L. Wallen, "Completely 'Green' Synthesis and Stabilization of Metal Nanoparticles," J. American Chemical Society, 125(2003)13940-13941.
Santinho et al., Influence of Formulation on the Physiochemical Properties of Casein Microparticles, Int'l J. Pharm., 186(1999)191-198.
Scholes, P.D., A.G.A. Coombes, L. Ilium, S.S. Savis, M. Vert, and M.C. Davies, "The Preparation of Sub-200 nm Poly(lactide-co-glycolide) Microspheres for Site-Specific Drug Delivery," J. Controlled Release, 25(1993)145-153.
Sjostrom, et al., Journal of Pharmaceutical Sciences, vol. 82, No. 6 Jun. 1993, pp. 584-589.
Sugimoto, I., K. Sasaki, A. Kuchiki, T. Ishihara, and H. Nakagawa, Chem. Pharm. Bull, 30:12(1982)4479-4488.
Suverkrup, R., S. Grunthal, O. Krasichkova, S. Maier, A. Weischselbaum, B. Neff, M. Diestelhorst, S. Dinslage, and A. Lux, "The Ophthalmic Lyophilisate Carrier System (OLCS): Development of a Novel Dosage Form, Freeze-Drying Technique, and In Vitro Quality Control Tests, "European J. Pharmaceutics and Biopharmaceutics, 57(2004)269-277.
Takayama, K., N. Nambu, and T. Nagai., Chem. Pharm. Bull., 30:2(1982)673-678.
Takenaka, H., Y. Kawashima and S.Y. Lin, J. Pharm. Sci., 69:12(1980)1388-1392.
Takeuchi, H., T. Handa and Y. Kawashima, Chem. Pharm. Bull., 35:9(1987)3800-3806.
Tuovinen, L., E. Ruhanen, T. Kinnarinen, S. Ronkko, J. Pelkonen, A. Urtti, S. Peltonen, and K. Jarvinen, "Starch Acetate Microparticles for Drug Delivery Into Retinal Pigment Epithelium—In Vitro Study," J. of Controlled Release, 98(2004)407-413.
Ueda, M., A. Iwara, and J. Kreuter, "Influence of the Preparation Methods on the Drug Release Behaviour of Loperamide-Loaded Nanoparticles," J. Microencapsulation, 15:3(1998)361-372.
University of Guelph, Dairy Chemistry and Physics, 2006, 16 pp.
Vandamme, Th.F., "Microemulsions as Ocular Drug Delivery Systems: Recent Developments and Future Challenges," Progress in Retinal and Eye Research, 21(2002)15-34.
Vandervoort, J., and A. Ludwig, "Preparation and Evaluation of Drug-Loaded Gelatin Nanoparticles for Topical Ophthalmic Use," European J. of Pharmaceutics and Biopharmaceutics, 57(2004)251-261.
Willmott et al., Doxorubicin-Loaded Casein Microspheres: Protean Nature of Drug Incorporation J. Pharm. Pharnnacol. 42(1992)472-475.
Zahr, A.S., M. de Villiers, and M.V. Pishko, "Encapsulation of Drug Nanoparticles in Self-Assembled Macromolecular Nanoshells," Langmuir, 21(2005)503 410.
Zimmer, A., and J. Kreuter, "Microspheres and Nanoparticles Used in Ocular Delivery Systems," Advanced Drug Delivery Reviews, 16(1995)61-73.

* cited by examiner

NANOPARTICLES COMPRISING A CHOLESTERYL ESTER TRANSFER PROTEIN INHIBITOR AND ANON-IONIZABLE POLYMER

CROSS REFERENCE TO RELATED APPLICATIONS

This is a 371 of PCT/IB/2007/001145 filed Apr. 23, 2008, and claims priority of U.S. 60/915,698 filed 3 May 2007.

BACKGROUND OF THE INVENTION

The present invention relates to nanoparticles comprising a poorly water-soluble cholesteryl ester transfer protein inhibitor (CETPI) and a poorly aqueous soluble non-ionizable polymer.

Atherosclerosis and its associated coronary artery disease (CAD) is the leading cause of death in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of this condition has been shown to be strongly correlated with certain plasma lipid levels. While elevated LDL-cholesterol may be the most recognized form of dyslipidemia, it is by no means the only significant lipid associated contributor to CHD. Low HDL-cholesterol is also a known risk factor for CHD (Gordon, D. J., et al., "High-density Lipoprotein Cholesterol and Cardiovascular Disease", Circulation, (1989), 79: 8-15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL cholesterol only modestly (±10-12%). As a result, there is a significant unmet medical need for a well-tolerated agent which can significantly elevate plasma HDL levels, thereby reversing or slowing the progression of atherosclerosis.

CETPIs have been developed which inhibit CETP activity, and thus, if present in the blood, should result in higher HDL cholesterol levels and lower LDL cholesterol levels. To be effective, such CETPIs must be absorbed into the blood. Oral dosing of CETPIs is preferred because to be effective such CETPIs must be taken on a regular basis, such as daily. Therefore, it is preferred that patients be able to take CETPIs by oral dosing rather than by injection.

CETPIs, particularly those that have high binding activity, are generally hydrophobic, have extremely low aqueous solubility and have low oral bioavailability when dosed conventionally. Such compounds have generally proven to be difficult to formulate for oral administration such that high bioavailabilities are achieved.

It is known that poorly water-soluble drugs may be formulated as nanoparticles. Nanoparticles are of interest for a variety of reasons, such as to improve the bioavailability of poorly water-soluble drugs, to provide targeted drug delivery to specific areas of the body, to reduce side effects, or to reduce variability in vivo.

A variety of approaches have been taken to formulate drugs as nanoparticles. One approach is to decrease the size of crystalline drug by grinding or milling the drug in the presence of a surface modifier. See, e.g., U.S. Pat. No. 5,145,684. Another approach to forming nanoparticles is to precipitate the drug in the presence of a film forming material such as a polymer. See, e.g., U.S. Pat. No. 5,118,528.

While these formulations may be functional for many classes of drugs, the very low water solubilities and lipophilic nature of CETPIs pose challenges when developing nanoparticle formulations. Accordingly, there is a continuing need to develop formulations of CETPIs that improve their bioavailability when dosed orally to certain mammalian species.

BRIEF SUMMARY OF THE INVENTION

In a first aspect, a pharmaceutical composition comprises nanoparticles, the nanoparticles comprising (a) a CETPI having an aqueous solubility of less than 1 mg/mL over the pH range of 6.5 to 7.5 at 25° C., at least 90 wt % of the CETPI in the nanoparticle being non-crystalline, and (b) a poorly aqueous soluble non-ionizable polymer; wherein the nanoparticles have an average size of less than 500 nm, and wherein the nanoparticles comprise a core, and the CETPI and the non-ionizable polymer collectively constitute at least 80 wt % of the core.

In one embodiment, the nanoparticles further comprise a surface stabilizer.

In another embodiment, the CETPI is selected from the group consisting of (2R)-3-[[3-(4-chloro-3-ethylphenoxy)phenyl][[3-(1,1,2,2-tetrafluoroethoxy)phenyl]methyl]amino]-1,1,1-trifluoro-2-propanol; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl)]-(2-methyl-2H-tetrazol-5-yl)-amine; and pharmaceutically acceptable forms thereof.

In still another embodiment, the CETPI is (2R)-3-[[3-(4-chloro-3-ethylphenoxy)phenyl][[3-(1,1,2,2-tetrafluoroethoxy)phenyl]methyl]amino]-1,1,1-trifluoro-2-propanol or a pharmaceutically acceptable form thereof.

In yet another embodiment, the non-ionizable polymer is selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(lactide), poly(glycolide), poly($\epsilon$-caprolactone), poly(lactide-co-glycolide), poly(lactide-co-$\epsilon$-caprolactone), poly(ethylene oxide-co-$\epsilon$-caprolactone), poly(ethylene oxide-co-lactide), and poly(ethylene oxide-co-lactide-co-glycolide), poly(isobutyl)cyanoacrylate, and poly(hexyl)cyanoacrylate.

In another embodiment, the non-ionizable polymer is selected from the group consisting of ethylcellulose and poly(ethylene oxide-co-$\epsilon$-caprolactone).

Nanoparticles comprising a CETPI and a poorly aqueous soluble non-ionizable polymer result in a material that improves the bioavailability of the CETPI when administered to an aqueous use environment.

Because the non-ionizable polymer is poorly aqueous soluble at physiological pH, the nanoparticles maintain the CETPI within a solid (or at least undissolved) polymer matrix when the nanoparticles are suspended in an aqueous solution.

The foregoing and other objectives, features, and advantages of the invention will be more readily understood upon consideration of the following detailed description of the invention.

DETAILED DESCRIPTION OF THE INVENTION

The nanoparticles of the present invention comprise a CETPI and a poorly aqueous soluble non-ionizable polymer. The nature of the nanoparticles, suitable CETPIs, suitable polymers, and methods for making nanoparticles are described in detail below.

Nanoparticles

The nanoparticles are small particles comprising a CETPI and the non-ionizable polymer. By "nanoparticles" is meant a plurality of small particles in which the average size of the particles in suspension is less than about 500 nm. By "average size" is meant the effective cumulant diameter as measured by dynamic light scattering, using for example, Brookhaven Instruments' 90Plus particle sizing instrument. By "size" is meant the diameter for spherical particles, or the maximum diameter for non-spherical particles. Preferably, the average size of the nanoparticles is less than 400 nm, more preferably less than 300 nm, more preferably less than 200 nm, more preferably less than 150 nm, and most preferably less than 100 nm.

The width of the particle size distribution in suspension is given by the "polydispersity" of the particles, which is defined as the relative variance in the correlation decay rate distribution, as is known by one skilled in the art. See B. J. Fisken, "Revisiting the method of cumulants for the analysis of dynamic light-scattering data," *Applied Optics*, 40(24), 4087-4091 (2001) for a discussion of cumulant diameter and polydispersity. Preferably, the polydispersity of the nanoparticles is less than 0.5. More preferably, the polydispersity of the nanoparticles is less than about 0.3. In one embodiment, the average size of the nanoparticles is less than 500 nm with a polydispersity of 0.5 or less. In another embodiment, the average size of the nanoparticles is less than 300 nm with a polydispersity of 0.5 or less. In still another embodiment, the average size of the nanoparticles is less than 200 nm with a polydispersity of 0.5 or less. In yet another embodiment, the average size of the nanoparticles is less than 200 nm with a polydispersity of 0.3 or less.

The nanoparticles can exist in a number of different configurations. In one embodiment, the nanoparticles comprise a core, the core comprising the CETPI and the poorly aqueous soluble non-ionizable polymer. As used herein, the term "core" refers to the interior portion of the nanoparticle. The nanoparticles also have a "surface portion," meaning the outside or exterior portion of the nanoparticle. Thus, the nanoparticles consist of a core (i.e., the interior portion) and a surface portion. In some embodiments, described herein below, materials may be adsorbed to the surface portion of the nanoparticle. Materials adsorbed to the surface portion of the nanoparticle are considered part of the nanoparticle, but are distinguishable from the core of the nanoparticle. Methods to distinguish materials present in the core versus materials adsorbed to the surface portion of the nanoparticle include (1) thermal methods, such as differential scanning calorimetry (DSC); (2) spectroscopic methods, such as X-ray photoelectron spectroscopy (XPS), transmission electron microscopy (TEM) with energy dispersive X-ray (EDX) analysis, fourier transform infra red (FTIR) analysis, and raman spectroscopy; (3) chromatographic techniques, such as high performance liquid chromatography (HPLC), and gel-permeation chromatography (GPC); and (4) other techniques known in the art.

In one embodiment, the CETPI and the poorly aqueous soluble non-ionizable polymer constitute at least 80 wt % of the core, more preferably at least 90 wt % of the core. In another embodiment, the core consists essentially of the CETPI and the poorly aqueous soluble non-ionizable polymer.

The CETPI present in the core can exist in pure CETPI domains, as a thermodynamically stable solid solution of the CETPI homogeneously distributed throughout the non-ionizable polymer, as a supersaturated solid solution of the CETPI homogeneously distributed throughout the non-ionizable polymer, or any combination of these states or those states that lie between them. When the glass-transition temperature ($T_g$) of the CETPI is different from the $T_g$ of the pure polymer by at least about 20° C., the core may exhibit a $T_g$ that is different than the $T_g$ of pure CETPI or pure polymer. Preferably, less than 20 wt % of the CETPI is present in pure CETPI domains, while the remaining CETPI is homogeneously distributed throughout the non-ionizable polymer.

In yet another embodiment, the core comprises the CETPI, the poorly aqueous soluble non-ionizable polymer, and an optional surface stabilizer. The core may be (1) a homogeneous molecular mixture of the CETPI, non-ionizable polymer, and optional surface stabilizer, (2) domains of pure the CETPI, domains of pure non-ionizable polymer, and domains of pure surface stabilizer distributed throughout the core, or (3) any combination of these states or those states that lie between them. In one embodiment, the CETPI, non-ionizable polymer, and surface stabilizer are homogeneously distributed throughout the core as a supersaturated solid solution. In another embodiment, the surface portion of the nanoparticle has a higher concentration of surface stabilizer relative to the nanoparticle as a whole.

In still another embodiment, the core comprises the CETPI and the poorly aqueous soluble non-ionizable polymer, with the surface stabilizer adsorbed to the surface portion of the nanoparticle.

In yet another embodiment, the core comprises the CETPI, the poorly aqueous soluble non-ionizable polymer, and a portion of the surface stabilizer. The remaining portion of the surface stabilizer is adsorbed to the surface portion of the nanoparticle. In this embodiment, a portion of the surface stabilizer is integral to the core, while the remaining portion of surface stabilizer is adsorbed to the surface portion of the nanoparticle.

At least 90 wt % of the CETPI is present in the nanoparticles in non-crystalline form. The term "crystalline," as used herein, means a particular solid form of a compound that exhibits long-range order in three dimensions. "Non-crystalline" refers to material that does not have long-range three-dimensional order, and is intended to include not only material which has essentially no order, but also material which may have some small degree of order, but the order is in less than three dimensions and/or is only over short distances. Another term for a non-crystalline form of a material is the "amorphous" form of the material. It is well known that the non-crystalline form of a low-solubility drug provides a greater aqueous concentration of drug relative to the crystalline form of the drug when administered to an aqueous use environment. However, it is also well known that when the drug is not stabilized in the non-crystalline form, the drug rapidly converts to the crystalline form in the use environment. See, for example, Hancock and Parks (*Pharmaceutical Research*, Vol. 17, No. 4, 2000). Thus, the poorly aqueous soluble non-ionizable polymer is selected to maintain the stability of the non-crystalline CETPI in the nanoparticle and while suspended in an aqueous solution, resulting in an enhanced concentration of free drug when the nanoparticle is administered to an aqueous use environment. Preferably at least 95 wt % of the CETPI in the nanoparticle is non-crystalline; in other words, the amount of CETPI in crystalline form is below detection limits and does not exceed about 5 wt %. Amounts of crystalline CETPI may be measured by Powder X Ray Diffraction (PXRD), by Differential Scanning Calorimetry (DSC), by solid-state nuclear magnetic resonance (NMR), or by any other known quantitative measurement.

In another embodiment, at least 95 wt % of the CETPI in the nanoparticle is non-crystalline, meaning that the compound exhibits no crystalline peaks when evaluated by PXRD. In another embodiment, the CETPI is not in a "semi-ordered" state and shows no long-range three-dimensional order when evaluated by PXRD.

The CETPI and the non-ionizable polymer are collectively present in the core in an amount ranging from about 80 wt % to 100 wt %. Preferably, the CETPI and the non-ionizable polymer collectively constitute at least 90 wt %, more preferably at least 95 wt % of the core. In one embodiment, the nanoparticles consist essentially of the CETPI, the non-ionizable polymer, and an optional surface stabilizer. By "consist essentially of" is meant that the nanoparticle contains less than 1 wt % of any other excipients and that any such excipients have no affect on the performance or properties of the nanoparticle.

The amount of CETPI in the nanoparticle may range from 0.1 wt % to 90 wt %. Preferably the amount of CETPI in the nanoparticle ranges from about 1 wt % to about 85 wt %, more preferably from about 5 wt % to about 80 wt %, even more preferably from about 10 wt % to about 75 wt %, and most preferably from about 25 wt % to about 75 wt %.

The amount of poorly aqueous soluble non-ionizable polymer may range from 10 wt % to 99.9 wt %. The physical stability of the CETPI in the nanoparticle tends to improve with increasing amounts of the poorly aqueous soluble non-ionizable polymer. Accordingly, it is preferred that the amount of poorly aqueous soluble non-ionizable polymer in the nanoparticle is at least 15 wt %, more preferably at least 20 wt %, and most preferably at least 25 wt %. However, too much non-ionizable polymer will lead to low CETPI loading in the nanoparticle. Thus, it is preferred that the amount of poorly aqueous soluble non-ionizable polymer in the nanoparticle is 75% or less, and most preferably 70 wt % or less.

The amount of optional surface stabilizer may range from 0 wt % to 40 wt %. When a surface stabilizer is present in the nanoparticle, it preferably constitutes at least 0.1 wt % of the total mass of the nanoparticle. Often, even greater amounts of surface stabilizer are desired. Thus, the surface stabilizer may constitute at least 1 wt %, 5 wt %, or even 10 wt % or more of the total mass of the nanoparticle. The surface stabilizer acts to reduce or prevent aggregation or flocculation of the nanoparticles in an aqueous suspension, resulting in nanoparticles with improved stability. Generally, lower concentrations of surface stabilizer are preferred. Thus, preferably the surface stabilizer constitutes about 35 wt % or less, more preferably about 30 wt % or less, and most preferably about 25 wt % or less the total mass of the nanoparticles.

Preferred embodiments of nanoparticles have the following amount of CETPI, poorly aqueous soluble non-ionizable polymer, and optional surface stabilizer:

5 to 80 wt % CETPI;
20 to 95 wt % poorly aqueous soluble non-ionizable polymer; and
0 to 40 wt % optional surface stabilizer.

In one embodiment, the nanoparticles comprise at least 20 wt % CETPI and at least 40 wt % of a poorly aqueous soluble non-ionizable polymer.

Cholesteryl Ester Transfer Protein Inhibitors

The CETPI may be any compound capable of inhibiting the cholesteryl ester transfer protein. The effect of a drug on the activity of CETP can be determined by measuring the relative transfer ratio of radiolabeled lipids between lipoprotein fractions, essentially as previously described by Morton in *J. Biol. Chem.* 256, 11992, 1981 and by Dias in *Clin. Chem.* 34, 2322, 1988, and as presented in U.S. Pat. No. 6,197,786, the disclosures of which are herein incorporated by reference. The potency of CETPIs may be determined by performing the above-described assay in the presence of varying concentrations of the test compounds and determining the concentration required for 50% inhibition of transfer of radiolabeled lipids between lipoprotein fractions. This value is defined as the "$IC_{50}$ value." Preferably, the CETP inhibitor has an $IC_{50}$ value of less than about 2000 nM, more preferably less than about 1500 nM, even more preferably less than about 1000 nM, and most preferably less than about 500 nM.

The CETPI is typically "sparingly water-soluble," which means that the CETPI has a solubility in water of less than 1 mg/mL over the pH range of 6.5 to 7.5 at 25° C. Many CETPIs are "substantially water-insoluble," which means that the CETPI has a solubility in water of less than 0.1 mg/mL. Compositions of the present invention find greater utility as the solubility of the CETPI decreases, and thus are preferred for CETPIs with solubilities less than about 0.1 mg/mL, more preferred for CETPIs with solubilities less than 0.01 mg/mL (10 µg/mL), and even more preferred for CETPIs with solubilities less than about 0.001 mg/mL (1 µg/mL). Many CETPIs have even lower solubilities (some less than 0.1 µg/mL), and require dramatic concentration enhancement to be sufficiently bioavailable upon oral dosing for effective plasma concentrations to be reached at practical doses. Alternatively, the CETPI has a solubility in water over the pH range of 6.5 to 7.5 of less than 10 µg/mL, more preferably less than 2 µg/mL, and even more preferably of less than 1 µg/mL.

In general, the CETPI has a dose-to-solubility ratio greater than about 100 mL, where the dose-to-solubility ratio may be determined by dividing the dose (in mg) by the water solubility (in mg/ml). Compositions of the present invention, as mentioned above, find greater utility as the solubility of the CETPI decreases and the dose increases. Thus, the compositions are preferred as the dose-to-solubility ratio increases, and thus are preferred for dose-to-solubility ratios of at least 1000 mL, and more preferred for dose-to-solubility ratios of at least 5,000 mL, and even more preferred for dose-to-solubility ratios of at least 10,000 mL.

The low solubility of CETPIs is primarily due to the hydrophobic nature of CETPIs. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. The Log P may be estimated experimentally by determining the ratio of the drug solubility in octanol to the drug solubility in water. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (J. Chem. Inf. Comput. Sci., 27, 21 (1987)); Viswanadhan's fragmentation method (J. Chem. Inf. Comput. Sci., 29, 163 (1989)); or Broto's fragmentation method (Eur. J. Med. Chem.-Chim. Theor., 19, 71 (1984). In general, Log P values for CETPIs are greater than about 4 and are often greater than about 5.

The compositions of the present invention are also suitable for CETPIs that have low melting points. In one embodiment, the CETPI has a melting point of 160° C. or less, preferably 150° C. or less, and more preferably 140° C. or less.

In the following, by "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs.

Specific examples of CETP inhibitors include [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester; (2R)-3-[[3-(4-chloro-3-ethylphenoxy)phenyl][[3-(1,1,2,2-tetrafluoroethoxy)phenyl]methyl]amino]-1, 1,1-trifluoro-2-propanol; S-[2-([[1-(2-ethylbutyl)cyclohexyl]carbonyl]amino)phenyl]2-methylpropanethioate; trans-4-[[[[2-[[[(3,5-bis(trifluoromethyl)phenyl]methyl](2-methyl-2H-tetrazol-5-yl)amino]methyl]-4-(trifluoromethyl) phenyl]ethylamino]methyl]-cyclohexaneacetic acid; trans-(4-{[N-(2-{[N'-[3,5-bis(trifluoromethyl)benzyl]-N'-(2-methyl-2H-tetrazol-5-yl)amino]methyl}-5-methyl-4-trifluoromethylphenyl)-N-ethylamino]methyl}cyclohexyl) acetic acid methanesulfonate; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide; methyl N-(3-cyano-5-trifluoromethylbenzyl)-[6-(N'-cyclopentylmethyl-N'-ethylamino)indan-5-ylmethyl]-carbamate; methyl (3-cyano-5-trifluoromethylbenzyl)-[6-(N-cyclopentylmethyl-N-ethylamino)indan-5-ylmethyl]-carbamate; ethyl 4-((3,5-bis(trifluoromethyl)phenyl)(2-methyl-2H-tetrazol-5-yl)methyl)-2-ethyl-6-(trifluoromethyl)-3,4-dihydroquinoxaline-1(2H)-carboxylate; tert-butyl 5-(N-(3,5-bis(trifluoromethyl)benzyl)acetamido)-7-methyl-8-(trifluoromethyl)-2,3,4,5-tetrahydrobenzo[b]azepine-1-carboxylate; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; the drugs disclosed in commonly owned U.S. patent application. Ser. Nos. 09/918,127 and 10/066,091, the disclosures of both of which are incorporated herein by reference; and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; JP 11049743; WO 0018721; WO 0018723; WO 0018724; WO 0017164; WO 0017165; WO 0017166; EP 992496; EP 987251; WO 9835937; JP 03221376; WO 04020393; WO 05095395; WO 05095409; WO 05100298; WO 05037796; WO 0509805; WO 03028727; WO 04039364; WO 04039453; WO 0633002; and U.S. Provisional Patent Application Nos. 60/781,488 and 60/780,993, both of which were filed on Mar. 10, 2006.

Thus, in one embodiment, the CETP inhibitor is selected from the group of compounds mentioned above. In another embodiment, the CETP inhibitor is selected from the group consisting of (2R)-3-[[3-(4-chloro-3-ethylphenoxy)phenyl][[3-(1,1,2,2-tetrafluoroethoxy)phenyl]methyl]amino]-1,1,1-trifluoro-2-propanol; trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-benzyl]-(2-methyl-2H-tetrazol-5-yl)-amine; and pharmaceutically acceptable forms thereof.

In still another embodiment, the CETP inhibitor is (2R)-3-[[3-(4-chloro-3-ethylphenoxy)phenyl][[3-(1,1,2,2-tetrafluoroethoxy)phenyl]methyl]amino]-1,1,1-trifluoro-2-propanol.

In still another embodiment, the CETP inhibitor is trans-(2R,4S)-2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide.

Non-ionizable Polymers

The nanoparticles of the present invention comprise a poorly aqueous soluble non-ionizable polymer. The term "polymer" is used conventionally, meaning a compound that is made of monomers connected together to form a larger molecule. A polymer generally consists of at least about 20 monomers connected together. Thus, the molecular weight of the polymer generally will be about 2000 daltons or more. The polymer should be inert, in the sense that it does not chemically react with the CETPI in an adverse manner, and should be pharmaceutically acceptable.

The polymer is a poorly aqueous soluble non-ionizable polymer. By "poorly aqueous soluble" is meant that the polymer has a solubility of less than 0.1 mg/mL when administered alone at a concentration of 0.2 mg/mL to a phosphate buffered saline solution (PBS) at pH 6.5. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. A test to determine whether the polymer is insoluble may be performed as follows. The polymer is initially present in bulk powder form with average particle sizes of greater than about 1 micron. The polymer alone is administered at a concentration of 0.2 mg/mL to the PBS solution and stirred for approximately 1 hour at room temperature. Next, a nylon 0.45 μm filter is weighed, and the polymer solution is filtered. The filter is dried overnight at 40° C., and weighed the following morning. The amount of polymer dissolved is calculated from the amount of polymer added to the PBS solution minus the amount of polymer remaining on the filter (mg). The non-ionizable polymer is considered to be poorly aqueous soluble if it has a solubility of less than 0.1 mg/mL in this test. Preferably, when administered at a concentration of 0.2 mg/mL to the pH 6.5 PBS, a poorly aqueous soluble non-ionizable polymer has a solubility of less than 0.07 mg/mL, more preferably less than 0.05 mg/mL, and most preferably less than 0.01 mg/mL.

To ease processing, it is preferred that the poorly aqueous soluble non-ionizable polymer be soluble in an organic solvent. Preferably the polymer has a solubility in an organic solvent of at least about 0.1 mg/mL, and preferably at least 1 mg/mL. Preferably the polymer is not crosslinked.

The polymer is "non-ionizable," meaning that the polymer possesses substantially no ionizable functional groups. By "substantially no ionizable functional groups" is meant that the number of ionizable groups covalently attached to the polymer is less than about 0.05 milliequivalents per gram of polymer. Preferably, the number is less than about 0.02 milliequivalents per gram of polymer. By "ionizable groups" is meant functional groups that are at least about 10% ionized over at least a portion of the physiologically relevant pH range of 1 to 8. Such groups have $pK_a$ values of about 0 to 9.

Poorly aqueous soluble non-ionizable polymers for use with the present invention include substituted cellulosics, and non-cellulosics. By "cellulosic" is meant a cellulose polymer that has been modified by reaction of at least a portion of the hydroxyl groups on the saccharide repeating units with a compound to form an ester or an ether substituent.

In order to be poorly aqueous soluble, the polymer must be hydrophobic, meaning that the polymer has a sufficient number of hydrophobic groups relative to hydrophilic groups. In a preferred embodiment, the poorly aqueous soluble non-ionizable cellulosic polymer has an ether- or ester-linked alkyl substituent. Suitable alkyl substituents include $C_1$ to $C_4$ alkyl groups. Exemplary ether-linked substituents include methyl, ethyl, propyl, and butyl groups. Exemplary ester-linked substituents include acetate, propionate, and butyrate groups.

In general, the hydrophobic substituent is present at a degree of substitution of at least 0.03.

Exemplary poorly aqueous soluble non-ionizable substituted polysaccharides include methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, and hydroxypropyl methylcellulose butyrate. Preferably the poorly aqueous soluble non-ionizable polymer is selected from the group consisting of ethyl cellulose, cellulose acetate, and cellulose acetate butyrate.

Exemplary poorly aqueous soluble non-ionizable non-polysaccharides include vinyl polymers and copolymers, such as poly(vinyl acetate), poly(vinyl acetate-co-vinyl alcohol), and poly(ethylene-co-vinyl acetate); polymethacrylate and polyacrylate polymers and copolymers, such as poly(ethyl acrylate-methyl methacrylate) (2:1 monomer ratio), available as EUDRAGIT® NE; polylactones, such as poly(lactide), poly(glycolide), poly(ε-caprolactone), and copolymers of these, including poly(lactide-co-glycolide), poly(lactide-co-ε-caprolactone), poly(ethylene oxide-co-ε-caprolactone), poly(ethylene oxide-co-lactide), and poly(ethylene oxide-co-lactide-co-glycolide); and poly(alkyl)cyanoacrylates, such as poly(isobutyl)cyanoacrylate, and poly(hexyl)cyanoacrylate.

Thus, in one embodiment, the poorly aqueous soluble non-ionizable polymer is selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, low-substituted hydroxypropyl cellulose, hydroxypropyl methylcellulose acetate, hydroxypropyl methylcellulose propionate, hydroxypropyl methylcellulose butyrate, poly(lactide), poly(glycolide), poly(ε-caprolactone), poly(lactide-co-glycolide), poly(lactide-co-ε-caprolactone), poly(ethylene oxide-co-ε-caprolactone), poly(ethylene oxide-co-lactide), poly(ethylene oxide-co-lactide-co-glycolide), poly(isobutyl)cyanoacrylate, and poly(hexyl)cyanoacrylate.

In another embodiment, the non-ionizable polymer is selected from the group consisting of ethylcellulose, cellulose acetate, cellulose propionate, cellulose butyrate, cellulose acetate butyrate, and poly(ethylene-oxide-co-ε-caprolactone).

In still another embodiment, the non-ionizable polymer is selected from the group consisting of ethylcellulose and poly(ethylene-oxide-co-ε-caprolactone).

In another embodiment, the non-ionizable polymer is ethylcellulose. In yet another embodiment, the non-ionizable polymer is poly(ethylene-oxide-co-ε-caprolactone).

Optional Surface Stabilizers

The nanoparticles of the present invention may optionally comprise a surface stabilizer in addition to the CETPI and the non-ionizable polymer. The purpose of the surface stabilizer is to reduce or prevent aggregation or flocculation of the nanoparticles in an aqueous suspension, resulting in nanoparticles with improved stability. In one embodiment, the surface stabilizer is used to stabilize the nanoparticles during the formation process. The stabilizer should be inert, in the sense that it does not chemically react with the CETPI in an adverse manner, and should be pharmaceutically acceptable.

In one embodiment, the surface stabilizer is an amphiphilic compound, meaning that it has both hydrophobic and hydrophilic regions. In another embodiment, the surface stabilizer is a surfactant, including anionic, cationic, zwitterionic, and non-ionic surfactants. Mixtures of surface stabilizers may also be used.

Exemplary surface stabilizers include casein, caseinates, polyvinyl pyrrolidone (PVP), polyoxyethylene alkyl ethers, polyoxyethylene stearates, polyoxyethylene castor oil derivatives, poly(ethylene oxide-propylene oxide) (also known as poloxamers), tragacanth, gelatin, polyethylene glycol, bile salts (such as salts of dihydroxy cholic acids, including sodium and potassium salts of cholic acid, glycocholic acid, and taurocholic acid), phospholipids (such as phosphatidyl cholines, including 1,2-diacylphosphatidylcholine also referred to as PPC or lecithin), sodium dodecylsulfate (also known as sodium lauryl sulfate), benzalkonium chloride, sorbitan esters, polyoxyethylene alkyl ethers, polyoxyethylene castor oil derivatives, polyoxyethylene sorbitan fatty acid esters (polysorbates), polyoxyethylene stearates, triethanolamine, sodium docusate, sodium stearyl fumarate, sodium cyclamate, and mixtures and pharmaceutically acceptable forms thereof.

Process for Making Nanoparticles

The nanoparticles may be formed by any process that results in formation of nanoparticles of a CETPI and a non-ionizable polymer. The CETPI used to form the nanoparticles may be in a crystalline or non-crystalline form; however, at least 90 wt % of the CETPI in the resulting nanoparticles is in non-crystalline form.

One process for forming nanoparticles is an emulsification process. In this process, the CETPI and polymer are dissolved in an organic solvent that is immiscible with an aqueous solution in which the CETPI and polymer are insoluble, forming an organic solution. Solvents suitable for forming the solution of dissolved CETPI and polymer can be any compound or mixture of compounds in which the CETPI and the polymer are mutually soluble and which is immiscible in the aqueous solution. As used herein, the term "immiscible" means that the organic solvent has a solubility in the aqueous solution of less than about 10 wt %, preferably less than about 5 wt %, and most preferably less than about 3 wt %. Preferably, the organic solvent is also volatile with a boiling point of 150° C. or less. Exemplary organic solvents include methylene chloride, trichloroethylene, tetrachloroethane, trichloroethane, dichloroethane, dibromoethane, ethyl acetate, phenol, chloroform, toluene, xylene, ethyl-benzene, methylethyl ketone, methyl-isobutyl ketone, and mixtures thereof. Preferred organic solvents are methylene chloride, ethyl acetate, benzyl alcohol, and mixtures thereof. The aqueous solution is preferably water.

Once the organic solution is formed, it is then mixed with the aqueous solution and homogenized to form an emulsion of fine droplets of the water immiscible solvent distributed throughout the aqueous phase. The volume ratio of organic solution to aqueous solution used in the process will generally range from 1:100 (organic solution:aqueous solution) to 2:3 (organic solution:aqueous solution). Preferably, the organic solution:aqueous solution volume ratio ranges from 1:9 to 1:2 (organic solution:aqueous solution). The emulsion is generally formed by a two-step homogenization procedure. The solution of the CETPI, polymer and organic solvent are first mixed with the aqueous solution using a rotor/stator or similar mixer to create a "pre-emulsion". This mixture is then further processed with a high-pressure homogenizer that subjects the droplets to very high shear, creating a uniform emulsion of very small droplets. A portion of the organic solvent is then removed forming a suspension of the nanoparticles in the aqueous solution. Exemplary processes for removing the organic solvent include evaporation, extraction, diafiltration, pervaporation, vapor permeation, distillation, and filtration.

Preferably, the organic solvent is removed to a level that is acceptable according to The International Committee on Harmonization (ICH) guidelines. Preferably, the concentration of organic solvent in the nanoparticle suspension is less than the solubility of the organic solvent in the aqueous solution. Even lower concentrations of organic solvent are preferred. Thus, the concentration of organic solvent in the nanoparticle suspension may be less than about 5 wt %, less than about 3 wt %, less than 1 wt %, and even less than 0.1 wt %.

Thus, in one embodiment, a process for forming nanoparticles comprises: (a) dissolving a CETPI and a poorly aqueous soluble non-ionizable polymer in an organic solvent to form an organic solution; (b) forming an aqueous solution, the CETPI being poorly soluble in the aqueous solution and the organic solvent being immiscible with the aqueous solution; (c) forming an emulsion comprising the organic solution and the aqueous solution; (d) removing the organic solvent to form a suspension of solid nanoparticles having an average size of less than 500 nm, wherein the CETPI and the non-ionizable polymer collectively constitute at least 80 wt % of the nanoparticles.

An alternative process to form the nanoparticles is a precipitation process. In this process, the CETPI and polymer are first dissolved in an organic solvent that is miscible with an aqueous solution in which the CETPI and polymer are poorly soluble to form an organic solution. The organic solution is mixed with the aqueous solution causing the nanoparticles to precipitate. Organic solvents suitable for forming the organic solution of dissolved CETPI and polymer can be any compound or mixture of compounds in which the CETPI and the polymer are mutually soluble and which is miscible in the aqueous solution. Preferably, the organic solvent is also volatile with a boiling point of 150° C. or less. Exemplary organic solvents include acetone, methanol, ethanol, tetrahydrofuran (THF), and dimethylsulfoxide (DMSO). Mixtures of solvents, such as 50% methanol and 50% acetone, can also be used, so long as the polymer and the CETPI are sufficiently soluble to dissolve the CETPI and polymer. Preferred organic solvents are methanol, acetone, and mixtures thereof.

The aqueous solution may be any compound or mixture of compounds in which the CETPI and polymer are sufficiently insoluble so as to precipitate to form nanoparticles. The aqueous solution is preferably water.

The organic solution and aqueous solution are combined under conditions that cause solids to precipitate as nanoparticles. The mixing can be by addition of a bolus or stream of organic solution to a stirring container of the aqueous solution. Alternately a stream or jet of organic solution can be mixed with a moving stream of aqueous solution. In either case, the precipitation results in the formation of a suspension of nanoparticles in the aqueous solution.

For the precipitation process, the amount of CETPI and polymer in the organic solution depends on the solubility of each in the organic solvent and the desired ratios of CETPI to polymer in the resulting nanoparticles. The solution may comprise from about 0.1 wt % to about 20 wt % dissolved solids. A dissolved solids content of from about 0.5 wt % to 10 wt % is preferred.

The organic solution:aqueous solution volume ratio should be selected such that there is sufficient aqueous solution in the nanoparticle suspension that the nanoparticles solidify and do not rapidly agglomerate. However, too much aqueous solution will result in a very dilute suspension of nanoparticles, which may require further processing for ultimate use. Generally, the organic solution:aqueous solution volume ratio should be at least 1:100, but generally should be less than 1:2

(organic solution:aqueous solution). Preferably, the organic solution:aqueous solution volume ratio ranges from about 1:20 to about 1:3.

Once the nanoparticle suspension is made, a portion of the organic solvent may be removed from the suspension using methods known in the art. Exemplary processes for removing the organic solvent include evaporation, extraction, diafiltration, pervaporation, vapor permeation, distillation, and filtration. Preferably, the solvent is removed to a level that is acceptable according to ICH guidelines. Thus, the concentration of solvent in the nanoparticle suspension may be less than about 10 wt %, less than about 5 wt %, less than about 3 wt %, less than 1 wt %, and even less than 0.1 wt %.

When the optional surface stabilizer is included in the nanoparticle composition, it may be added to either the organic solution or the aqueous solution for either of the processes described above.

Thus, in another embodiment, a process for forming nanoparticles comprises: (a) forming an organic solution comprising a CETPI and a poorly aqueous soluble non-ionizable polymer dissolved in an organic solvent; (b) forming an aqueous solution, wherein the CETPI and the non-ionizable polymer are poorly soluble in the aqueous solution; (c) mixing the organic solution with the aqueous solution to form a first mixture; (d) removing the solvent from the first mixture to form a suspension comprising the nanoparticles and the aqueous solution, wherein (i) the nanoparticles have an average size of less than 500 nm; (ii) at least 90 wt % of the CETPI in the nanoparticle is in a non-crystalline form; and (iii) the nanoparticles comprising a core, wherein the CETPI and the non-ionizable polymer, collectively constitute at least 80 wt % of the core.

Both the emulsion process and the precipitation process result in the formation of a suspension of the nanoparticles in the aqueous solution. In some instances it is desirable to concentrate the nanoparticles or to isolate the nanoparticles in solid form by removing some or all of the liquid from the suspension. Exemplary processes for removing at least a portion of the liquid include spray drying, spray coating, spray layering, lyophylization, evaporation, vacuum evaporation, filtration, ultrafiltration, reverse osmosis, and other processes known in the art. Preferably, the liquid is removed by a process selected from spray drying, evaporation, and lyophylization. In one embodiment, the liquid is removed by spray drying. In another embodiment, the liquid is removed by evaporation. In still another embodiment, the liquid is removed by lyophylization. In yet another embodiment, the liquid is removed by a combination of processes selected from the group consisting of spray drying, spray coating, spray layering, lyophylization, evaporation, vacuum evaporation, filtration, ultrafiltration, and reverse osmosis. For example, the liquid may be removed by ultrafiltration, followed by spray drying, followed by evaporation in a tray dryer.

When isolating the nanoparticles in solid form, it is often desirable to include a matrix material in the suspension of nanoparticles prior to removal of the liquid. The matrix material functions to help slow or prevent agglomeration of the nanoparticles as the liquid is being removed, as well as to help re-suspend the nanoparticles when the solid composition is added to an aqueous solution (e.g., an aqueous environment of use). The matrix material is preferably pharmaceutically acceptable and water soluble. Examples of matrix materials include polyvinyl pyrrolidone (PVP), trehalose, hydroxypropyl methyl cellulose (HPMC), hydroxypropyl cellulose (HPC), casein, caseinate, albumin, gelatin, acacia, lactose, mannitol, other matrix materials know in the art, and pharmaceutically acceptable forms and mixtures thereof.

The amount of matrix material present with the nanoparticles will depend on the matrix material used and the nanoparticle composition. Generally, the mass ratio of nanoparticles to matrix material ranges from 9:1 to 1:9 (that is, 10 wt % matrix material to 90 wt % matrix material relative to the total mass of nanoparticles and matrix material in the composition). Preferably the mass ratio of nanoparticle to matrix material is at least 4:1, and more preferably at least 3:1. However, too much matrix material leads to low amounts of CETPI in the composition. Thus, the mass ratio of nanoparticles to matrix material is preferably less than 1:4, and most preferably less than 1:3.

In one embodiment of the invention, a solid composition comprises (a) a plurality of nanoparticles comprising a CETPI and a poorly aqueous soluble non-ionizable polymer, and (b) a matrix material. As used herein, the term "solid pharmaceutical composition" means that the composition is in a solid form and substantially free of liquids. The nanoparticles are entrapped or encapsulated in the matrix material.

In another embodiment, a composition comprises nanoparticles and a matrix material, wherein a mass ratio of the nanoparticles to the matrix material ranges from 9:1 to 1:9.

In still another embodiment, the matrix material is casein or a pharmaceutically acceptable form thereof.

Dosage Forms

The nanoparticles may be administered using any known dosage form. The nanoparticles may be formulated for administration via oral, topical, subdermal, intranasal, buccal, intrathecal, ocular, intraaural, intraarticular, subcutaneous spaces, vaginal tract, arterial and venous blood vessels, pulmonary tract or intramuscular tissue of an animal, such as a mammal and particularly a human. Oral dosage forms include: powders or granules; tablets; chewable tablets; capsules; unit dose packets, sometimes referred to in the art as "sachets" or "oral powders for constitution" (OPC); syrups; and suspensions.

In one embodiment, the compositions of the present invention are capable of improving the concentration of dissolved CETPI in a use environment relative to a control composition consisting essentially of the CETPI alone without the polymer. In order to determine concentration enhancement in vitro, the amount of "free" CETPI, or solvated CETPI is measured. By "free" CETPI is meant CETPI which is dissolved or present in micelles, but which is not in the nanoparticles or any solid particles larger than 500 nm, such as precipitate. A composition of the invention provides concentration enhancement if, when administered to an aqueous use environment, it provides a free CETPI concentration that is at least 1.25-fold the free CETPI concentration provided by the control composition. Preferably, the free CETPI concentration provided by the compositions of the invention are at least about 1.5-fold, more preferably at least about 2-fold, and most preferably at least about 3-fold that provided by the control composition.

Alternatively, the compositions of the present invention, when dosed orally to a mammalian subject such as a human, provide an AUC in CETPI concentration, in the blood plasma or serum (or relative bioavailability) that is at least 1.25-fold that observed in comparison to the control composition. Preferably, the blood AUC is at least about 2-fold, more preferably at least about 3-fold, even more preferably at least about 4-fold, still more preferably at least about 6-fold, yet more preferably at least about 10-fold, and most preferably at least about 20-fold that of the control composition. The determination of AUCs is a well-known procedure and is described, for example, in Welling, "Pharmacokinetics Processes and Mathematics," ACS Monograph 185 (1986).

Alternatively, the compositions of the present invention, when dosed orally to a mammalian subject such as a human, provide a maximum CETPI concentration in the blood plasma or serum ($C_{max}$) that is at least 1.25-fold that observed in comparison to the control composition. Preferably, the $C_{max}$ is at least about 2-fold, more preferably at least about 3-fold, even more preferably at least about 4-fold, still more preferably at least about 6-fold, yet more preferably at least about 10-fold, and most preferably at least about 20-fold that of the control composition. Thus, compositions that meet the in vitro or in vivo performance criteria, or both, are considered to be within the scope of the invention.

Without further elaboration, it is believed that one of ordinary skill in the art can, using the foregoing description, utilize the present invention to its fullest extent. Therefore, the following specific embodiments are to be construed as merely illustrative and not restrictive of the scope of the invention. Those of ordinary skill in the art will understand that variations of the conditions and processes of the following examples can be used.

EXAMPLES

Drugs Used in Examples

The following drugs were used in the examples described below.

Drug 1 was (2R)-3-[[3-(4-chloro-3-ethylphenoxy)phenyl][[3-(1,1,2,2-tetrafluoroethoxy)phenyl]methyl]amino]-1,1,1-trifluoro-2-propanol, having the structure:

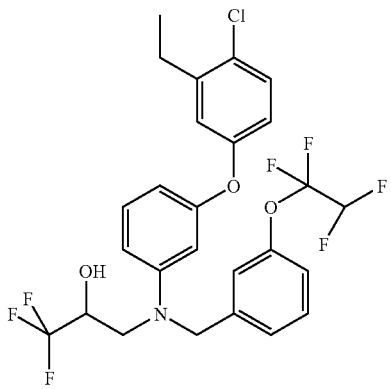 [SMILES: CCc1cc(Oc2cccc(N(Cc3cccc(OC(F)(F)C(F)F)c3)CC(O)C(F)(F)F)c2)ccc1Cl]

Drug 1 has a solubility in phosphate buffered saline at pH 6.5 (PBS) of less than 0.1 µg/mL, and a CLog P value of 9.8. The $T_m$ of Drug 1 is 10° C., and the $T_g$ was determined by DSC analysis to be −16° C.

Drug 2 was [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, having the structure:

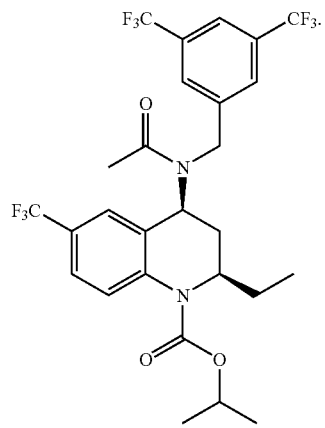 [SMILES: CC[C@@H]1C[C@H](N(Cc2cc(C(F)(F)F)cc(C(F)(F)F)c2)C(C)=O)c2cc(C(F)(F)F)ccc2N1C(=O)OC(C)C]

Drug 2 has a solubility in model fasted duodenal (MFD) solution of about 11 µg/mL, and a CLog P value of about 6.6. The $T_m$ of Drug 2 is 111° C., and the $T_g$ was determined by DSC analysis to be about 45° C.

Drug 3 was [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib, having the structure:

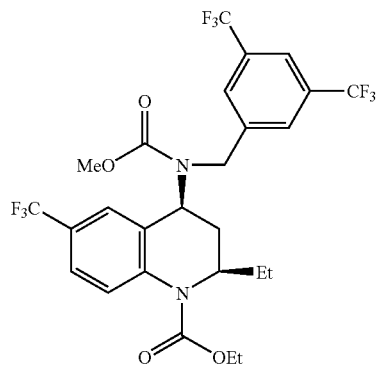 [SMILES: CCOC(=O)N1c2ccc(C(F)(F)F)cc2[C@@H](N(Cc2cc(C(F)(F)F)cc(C(F)(F)F)c2)C(=O)OC)C[C@H]1CC]

Drug 3 has a solubility in water of less than 0.1 µg/mL, and a CLog P value of 7.6. The $T_m$ of Drug 3 is 99° C., and the $T_g$ was determined by DSC analysis to be 29° C.

Polymers Used in Examples

The following poorly aqueous soluble non-ionizable polymers were used in the examples: ethylcellulose (ETHOCEL® Viscosity 4, Dow Chemical Co., Midland, Mich.); and poly(ethylene oxide-co-ε-caprolactone), designated as pCL-PEG (grade P3128-EOCL available from Polymer Source Inc., Montreal, Quebec, Canada), having an ε-polycaprolactone molecular weight of 10,000 Daltons and a poly(ethylene oxide) molecular weight of 5,000 Daltons.

The polymers were evaluated using the following procedure to determine their aqueous solubility. First, 0.2 mg/mL of the polymer was added to a PBS solution consisting of 20 mM $Na_2HPO_4$, 47 mM $KH_2PO_4$, 87 mM NaCl, and 0.2 mM KCl, adjusted to pH 6.5 with NaOH. The polymer was stirred in the PBS solution for approximately 1 hour at room temperature. Next, the polymer solution was filtered through a nylon 0.45 µm filter that had been weighed dry prior to filtration. The filter was dried overnight at 40° C., and weighed the following morning. The amount of soluble polymer was calculated from the amount of polymer added to form the polymer solution minus the amount of polymer remaining on the filter. The results of these tests are shown in Table 1 and show that all of the polymers tested are poorly aqueous soluble.

TABLE 1

| Example Polymer | Soluble at pH 6.5 (mg/mL) | Observations |
|---|---|---|
| Ethylcellulose | <0.001 | Fine particle suspension |
| pCL-PEG | 0.02 | Fine particle suspension |

Example 1

Nanoparticles containing Drug 1 were made using the following procedure. First, 300 mg Drug 1 and 300 mg ethylcellulose were dissolved in 7.5 mL ethyl acetate. The organic solution was then poured into 30 mL of water and the mixture was emulsified for 3 min using a Kinematica Polytron 3100 rotor/stator (Kinematica AG, Lucerne, Switzerland) at 10,000 rpm (high-shear mixing). The solution was further emulsified using a Microfluidizer (Microfluidics [Newton, Mass.] model M-110S F12Y with ice bath and cooling coil), for 6 minutes (high-pressure homogenization). The ethyl acetate was removed from the emulsion using a rotary evaporator, resulting in an aqueous suspension of nanoparticles consisting of 50 wt % Drug 1 and 50 wt % ethylcellulose.

Light Scattering Analysis

The particle size of the nanoparticles in the aqueous suspension was determined using dynamic light scattering (DLS) as follows. First, the aqueous suspension was filtered using a 1 μm glass membrane filter (Anatop filter, Whatman), and poured into a cuvette. Light-scattering was measured using a Brookhaven Instruments (Holtsville, N.Y.) BI-200SM particle size analyzer with a BI-9000AT correlator. The sums of exponentials from the autocorrelation functions are analyzed to extract size distributions from the samples, and the size is reported as the cumulant value. The average diameter was found to be 178 nm, with a polydispersity of 0.12.

Example 2

For Example 2, nanoparticles containing Drug 1 were prepared using the procedures described in Example 1 with the following exceptions. The organic solution contained 300 mg Drug 1 and 300 mg pCL-PEG in 7.5 mL ethyl acetate. This organic solution was mixed with 30 mL deionized water and emulsified using the procedures outlined in Example 1 to form nanoparticles having a cumulant diameter of 117 nm and a polydispersity of 0.19.

Example 3

Nanoparticles containing Drug 2 were prepared as follows. First, 120 mg Drug 2 and 420 mg ethylcellulose were dissolved in 7.5 mL methylene chloride to form an organic solution. Next, 60 mg sodium taurocholate (NaTC, a surface stabilizer) was added to 30 mL deionized water to form an aqueous solution. The organic solution was then poured into the aqueous solution and emulsified as described in Example 1. The methylene chloride was removed from the emulsion using a rotary evaporator, resulting in an aqueous suspension of nanoparticles, with a composition ratio of 20:70:10 Drug 2:ethylcellulose:NaTC. DLS analysis showed that the average cumulant diameter of the nanoparticle suspension was 64 nm, with a polydispersity of 0.20.

Example 4

Nanoparticles containing Drug 2 were prepared using the procedures described in Example 1 with the following exceptions. The organic solution consisted of 20 mg Drug 2 and 30 mg ethylcellulose dissolved in 4 mL methylene chloride, while the aqueous solution consisted of 40 mg NaTC dissolved in 20 mL deionized water. The organic solution was then poured into the aqueous solution and emulsified as described for Example 1, except that the high shear mixing time was reduced to 2 minutes. The methylene chloride was removed from the emulsion using a rotary evaporator, resulting in an aqueous suspension of nanoparticles, with a composition ratio of 2:3:4 Drug 2:ethylcellulose:NaTC. DLS analysis showed that the average cumulant diameter of the nanoparticle suspension was 147 nm with polydispersity of 0.40.

Examples 5-7

Nanoparticles were made containing Drug 2 using the procedures described in Example 1 with the following exceptions. For the nanoparticles of Example 5, the organic solution consisted of 12.0 mg Drug 2 and 108.4 mg ethylcellulose dissolved in 11 mL methylene chloride, while the aqueous solution consisted of 19.8 mg NaTC dissolved in 20 mL deionized water. For Example 6, the organic solution consisted of 30.1 mg Drug 2 and 90.2 mg ethylcellulose dissolved in 11 mL methylene chloride, while the aqueous solution consisted of 20 mg NaTC dissolved in 20 mL deionized water. For Example 7, the organic solution consisted of 59.7 mg Drug 2 and 66.0 mg ethylcellulose dissolved in 11 mL methylene chloride, while the aqueous solution consisted of 19.4 mg NaTC dissolved in 20 mL deionized water. In all cases, the methylene chloride was removed from the emulsions using a rotary evaporator, resulting in aqueous suspensions of nanoparticles.

DLS analysis of the aqueous suspensions was performed as described in Example 1 and the results are presented in Table 2. The suspensions were also allowed to stand unmixed for 3 days at ambient conditions and the diameter of the nanoparticles was again measured by DLS. The results, shown in Table 2, indicate that no significant agglomeration of the nanoparticles had occurred.

TABLE 2

| Sample (wt:wt:wt Drug 2:Ethylcellulose:NaTC) | Initial | | After Storage for 3 Days Ambient | |
|---|---|---|---|---|
| | Cumulant Diameter (nm) | Poly-dispersity | Cumulant Diameter (nm) | Poly-dispersity |
| Example 5 (8.6:77.3:14.1) | 102 | 0.15 | 102 | 0.13 |
| Example 6 (21.4:64.3:14.3) | 93 | 0.18 | 92 | 0.16 |
| Example 7 (41.1:45.5:13.4) | 91 | 0.12 | 93 | 0.13 |

Examples 8-11

Nanoparticles containing Drug 3 were prepared using the procedures described in Example 1 with the following exceptions. For the nanoparticles of Example 8, the organic solution consisted of 94.397 mg Drug 3 and 94.592 mg ethylcellulose dissolved in 5 mL methylene chloride, and the aqueous solution consisted of 11.846 mg NaTC dissolved in 20 mL deionized water. For the nanoparticles of Example 9, the organic solution consisted of 141.634 mg Drug 3 and 47.379 mg ethylcellulose dissolved in 5 mL methylene chloride, and the aqueous solution consisted of 11.904 mg NaTC dissolved in 20 mL deionized water. For the nanoparticles of Example 10, the organic solution consisted of 111.538 mg Drug 3 and 66.938 mg ethylcellulose dissolved in 5 mL methylene chloride, and the aqueous solution consisted of 22.210 mg NaTC dissolved in 20 mL deionized water. For the nanoparticles of Example 11, the organic solution consisted of 80 mg Drug 3 and 80 mg ethylcellulose dissolved in 5 mL methylene chloride, and the aqueous solution consisted of 40 mg NaTC dissolved in 20 mL deionized water. The methylene chloride was removed from the emulsions using a rotary evaporator, resulting in aqueous suspensions of nanoparticles.

Light Scattering Analysis

DLS analysis of the aqueous suspensions was performed as described in Example 1 and the results are presented in Table 3. The suspensions were also allowed to stand unmixed for 24 hours at ambient conditions and the diameter of the nanoparticles was again measured by DLS. The results, shown in Table 3, indicate that no significant agglomeration of the nanoparticles had occurred.

TABLE 3

| Sample | Initial | | After Storage for 24 Hours Ambient | |
|---|---|---|---|---|
| (wt:wt:wt Drug 3:ethylcellulose:NaTC) | Diameter (nm) | Poly-dispersity | Diameter (nm) | Poly-dispersity |
| Example 8 (47:47:6) | 99 | 0.22 | 101 | 0.19 |
| Example 9 (71:23:6) | 101 | 0.21 | 104 | 0.16 |
| Example 10 (56:33:11) | 78 | 0.26 | 81 | 0.27 |
| Example 11 (40:40:20) | 71 | 0.30 | 77 | 0.33 |

Example 12

Nanoparticles containing Drug 2 were prepared using a precipitation procedure as follows. First, an organic solution was prepared by dissolving 20 mg Drug 2 and 180 mg ethylcellulose in 20 mL acetone. A 1-mL sample of this organic solution was then added to 9 mL water, resulting in a suspension of nanoparticles in the aqueous solution. DLS analysis showed that the nanoparticles had an effective diameter of 123 nm, with a polydispersity of 0.36. After storage at ambient conditions for 24 hours, the nanoparticles had an effective diameter of 120 nm, with a polydispersity of 0.32, indicating that no significant agglomeration of the nanoparticles had occurred.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A pharmaceutical composition comprising nanoparticle cores having an average size of less than 500 nm, said cores comprising:
    (a) a cholesteryl ester transfer protein inhibitor (CETPI) having a solubility in water of less than 1 mg/mL over the pH range of 6.5 to 7.5 at 25° C., at least 90 wt % of said CETPI in said nanoparticle being non-crystalline; and
    (b) a poorly aqueous soluble non-ionizable polymer selected from the group consisting of methylcellulose, ethylcellulose, propylcellulose, butylcellulose, cellulose acetate, cellulose propionate, cellulose butyrate, cellulose acetate butyrate, cellulose acetate propionate, methyl cellulose acetate, methyl cellulose propionate, methyl cellulose butyrate, ethyl cellulose acetate, ethyl cellulose propionate, ethyl cellulose butyrate, poly(lactide), poly(glycolide), poly(ε-caprolactone), poly(lactide-co-glycolide), poly(lactide-co-ε-caprolactone), poly(ethylene oxide-co-ε-caprolactone), poly(ethylene oxide-co-lactide), poly(ethylene oxide-co-lactide-co-glycolide), poly(isobutyl)cyanoacrylate, and poly(hexyl)cyanoacrylate;

wherein said CETPI and said non-ionizable polymer collectively constitute at least 80 wt % of said cores.

2. The composition of claim 1 wherein said CETPI and said non-ionizable polymer collectively constitute at least 90 wt % of said cores.

3. The composition of claim 1 wherein said cores consist essentially of said CETPI and said non-ionizable polymer.

4. The composition of claim 1 wherein said cores have the following composition: from 5 wt % to 80 wt % of said CETPI and from 20 wt % to 95 wt % of said non-ionizable polymer.

5. The composition of claim 1 wherein said cores have an average size of less than 300 nm.

6. The composition of claim 5 wherein said average size of said cores is less than 100 nm.

7. The composition of claim 1 wherein said non-ionizable polymer is selected from the group consisting of ethylcellulose and poly(ethylene oxide-co-ε-caprolactone).

8. The composition of claim 1 wherein said nanoparticle cores include a surface portion.

9. The composition of claim 8 further comprising a surface stabilizer adsorbed to said surface portion.

10. The composition of claim 9 wherein said surface stabilizer constitutes from 0.1 to 40 wt % of said nanoparticle cores.

11. The composition of claim 1 wherein said CETPI is selected from the group consisting of (2R)-3-[[3-(4-chloro-3-ethylphenoxy)phenyl][[3-(1,1,2,2-tetrafluoroethoxy)phenyl]methyl]amino]-1,1,1-trifluoro-2-propanol; trans -(2R,4S)- 2-(4-{4-[(3,5-bis-trifluoromethyl-benzyl)-(2-methyl-2H-tetrazol-5-yl)-amino]-2-ethyl-6-trifluoromethyl-3,4-dihydro-2H-quinoline-1-carbonyl}-cyclohexyl)-acetamide amine; (3,5-bis-trifluoromethyl-benzyl)-[2-(cyclohexyl-methoxy-methyl)-5-trifluoromethyl-benzyl]-(2-methyl-2H-tetrazol-5-yl)-amine; 1-[1-(2-{[(3,5-bis-trifluoromethyl-benzyl)-(2-methyl-2H-tetrazol-5-yl)-amino]-methyl}-4-trifluoromethyl-phenyl)-2-methyl-propyl]-piperidine-4-carboxylic acid; (3,5-bis-trifluoromethyl-benzyl)-[2-(1-methoxy-cycloheptyl)-5-trifluoromethyl-benzyl]-(2-methyl-2H-tetrazol-5-yl)-amine; (3,5-bis-trifluoromethyl-benzyl)-[2-(1-cyclohexyl-1-methoxy-ethyl)-5-trifluoromethyl-ethyl-benzyl]-(2-methyl-2H-tetrazol-5-yl)-amine; and pharmaceutically acceptable forms thereof.

12. The composition of claim 1 wherein said CETPI is (2R)-3-[[3-(4-chloro-3-ethylphenoxy)phenyl][[3-(1,1,2,2-tetrafluoroethoxy) phenyl]methyl]amino]-1,1,1-trifluoro-2-propanol or a pharmaceutically acceptable form thereof.

13. A pharmaceutical composition comprising an aqueous suspension of the nanoparticle cores of claim 1.

14. A pharmaceutical composition comprising the nanoparticle cores of claim 1 and a matrix material, wherein the mass ratio of said cores to said matrix material ranges from 9:1 to 1:9.

15. The composition of claim 10 wherein said surface stabilizer is selected from the group consisting of casein, caseinates, polyvinyl pyrrolidone, polyoxyethylene alkyl ethers, polyoxyethylene stearates, polyoxyethylene castor oil derivatives, poly(ethylene oxide-propylene oxide), tragacanth, gelatin, polyethylene glycol, sodium and potassium salts of cholic acid, glycocholic acid, and taurocholic acid, phospholipids, sodium dodecylsulfate, benzalkonium chloride, sorbitan esters, polyoxyethylene alkyl ethers, polyoxyethylene castor oil derivatives, polyoxyethylene sorbitan fatty acid esters, polyoxyethylene stearates, triethanolamine, sodium docusate, sodium stearyl fumarate, sodium cyclamate, and pharmaceutically acceptable forms and mixtures thereof.

* * * * *